United States Patent
Bernhard et al.

(10) Patent No.: US 10,898,454 B2
(45) Date of Patent: Jan. 26, 2021

(54) PROPHYLAXIS AND TREATMENT OF PRETERM BIRTH ASSOCIATED BRONCHOPULMONARY DYSPLASIA (BPD)

(71) Applicant: Eberhard Karls Universitaet Tuebingen Medizinische Fakultaet, Tuebingen (DE)

(72) Inventors: Wolfgang Bernhard, Rottenburg am Neckar (DE); Axel Franz, Tuebingen (DE)

(73) Assignee: EBERHARD KARLS UNIVERSITAET TUEBINGEN MEDIZINISCHE FAKULTAET, Tuebingen (DE)

( * ) Notice: Subject to any disclaimer, the term of this patent is extended or adjusted under 35 U.S.C. 154(b) by 0 days.

(21) Appl. No.: 15/663,483

(22) Filed: Jul. 28, 2017

(65) Prior Publication Data
US 2017/0326082 A1 Nov. 16, 2017

Related U.S. Application Data

(63) Continuation of application No. PCT/EP2016/051978, filed on Jan. 29, 2016.

(30) Foreign Application Priority Data

Jan. 29, 2015 (DE) ........................ 10 2015 101 273

(51) Int. Cl.
| | | |
|---|---|---|
| *A61K 31/14* | (2006.01) | |
| *A61K 31/202* | (2006.01) | |
| *G01N 33/92* | (2006.01) | |
| *A23L 33/10* | (2016.01) | |

(52) U.S. Cl.
CPC .............. *A61K 31/14* (2013.01); *A23L 33/10* (2016.08); *A61K 31/202* (2013.01); *G01N 33/92* (2013.01); *G01N 2800/38* (2013.01)

(58) Field of Classification Search
CPC .................................................... A61K 31/14
See application file for complete search history.

(56) References Cited

U.S. PATENT DOCUMENTS 6,753,350 B1 * 6/2004 Hansen .................. A61K 31/20
514/560

FOREIGN PATENT DOCUMENTS

| CA | 2 734 312 A1 | 9/2012 |
|---|---|---|
| WO | WO 98/36745 A1 | 8/1998 |
| WO | WO 2009/079544 A1 | 6/2009 |
| WO | WO 2012/125020 A1 | 9/2012 |

OTHER PUBLICATIONS

Wemhoner et al (BMC Pulmonary Medicine 2011, 11:7) (Year: 2011).*
Maas et al (Eur J Nutr (2017) 56:1733-1742) (Year: 2017).*
Dr. John Jones (https://www.nutritionpureandsimple.com/Images/PDF%20Articles/PerinatalNutrition.pdf accessed Mar. 8, 2018).*
Koletzko et al (Eur J Nutr 42 : 243-253 (2003)) (Year: 2003).*
Agostini et al. 2010 "Enteral Nutrient Supply for preterm infants: Commentary from the European Society of Paediatric Gastroenterology, Hepatology and Nutrition Committee on Nutrition" *J Ped Gastrenterology and Nutrition* 50: 85-91.
Bernhard et al. 2014 "Plasma phospholipids indicate impaired fatty acid homeostasis in preterm infants" *European Journal of Nutrition* 53: 1533-1547.
Bernhard et al. 2013 "Choline supply of preterm infants: assessment of dietary intake and pathophysiological considerations" *European Journal of Nutrition* 52(3):1269-1278.
Bernhard et al. 2014 "Choline concentrations are lower in postnatal plasma of preterm infants than in cord plasma" *European Journal of Nutrition* 54(5):733-41.
Harris et al. 2014 "Beyond building better brains: bridging the docosahexaenoic acid (DHA) gap of prematurity" *J Perinatol* 35(1):1-7.
Kibbe et al. 2000 Handbook of Pharmaceutical Excipients, 3$^{rd}$ Sub Edition, American Pharmaceutical Association and Pharmaceutical Press ( in 8 pages).
Zhang et al. 2014 "Omega-3 long-chain polyunsaturated fatty acids for extremely preterm infants: a systematic review" *Pediatrics* 134(1):120-34.

* cited by examiner

*Primary Examiner* — Kevin E Weddington (74) *Attorney, Agent, or Firm* — Knobbe, Martens, Olson & Bear, LLP (57) ABSTRACT

A composition for the prophylaxis and/or treatment of a developmental disorder which is associated with preterm birth, and a method for the diagnosis and/or determination and/or prediction of the degree of severity of a developmental disorder which is associated with preterm birth.

8 Claims, 5 Drawing Sheets

PROPHYLAXIS AND TREATMENT OF PRETERM BIRTH ASSOCIATED BRONCHOPULMONARY DYSPLASIA (BPD)

CROSS-REFERENCES TO RELATED APPLICATIONS

This application is a continuation of copending International Patent Application PCT/EP2016/051978, filed on 29 Jan. 2016 and designating the United States, which was not published under PCT Article 21(2) in English, and claims priority from German Patent Application DE 10 2015 101 273.1, filed on 29 Jan. 2015, which are both incorporated herein by reference.

FIELD OF THE INVENTION

The present invention relates to a method for the prophylaxis and/or treatment of a developmental disorder which is associated with preterm birth, and to a method for the diagnosis and/or determination and/or prediction of the degree of severity of a developmental disorder which is associated with preterm birth, and further subject matter associated therewith.

BACKGROUND OF THE INVENTION

According to an actual study of the WHO one out of ten babies world-wide is born too early. The number is increasing in almost all countries. In Germany the rate of preterm infants is about 9.2 children per 100. Each year in Germany about 63,000 children are born before the 37th week of pregnancy. 3,000 out of them are very early preterm infants which are born prior to the 30th pregnancy week.

Premature babies very often suffer from various health problems due to developmental disorders. Of particular relevance and critical for survival is degree of maturity of the lung. But also disruptions of the brain and/or eye developments can be observed.

RELATED PRIOR ART

Bernhard et al. (2013), Choline supply of preterm infants: assessment of dietary intake and pathophysiological considerations, Eur. J. Nutr. 52(3):1269-78; Bernhard et al. (2014), Plasma phospholipids indicate impaired fatty acid homeostasis in preterm infants, Eur. J. Nutr. 53(7):1533-47; Bernhard et al. (2014), Choline concentrations are lower in postnatal plasma of preterm infants than in cord plasma, Eur. J. Nutr., 23 Aug. 2014, Epub ahead of print, have established by means of descriptive examinations that preterm infants apparently have an undersupply of choline and a disorder of the fatty acid homeostasis.

The bronchopulmonary dysplasia (BPD) is a chronic lung disease which mainly arises in premature children with very low weight at birth. It may result in a longwinded damage of the lung up to early adulthood, or in case of a progressive pulmonary change it may lead to death. A premature lung with a lack of surfactant is a significant risk factor which is responsible for BPD. Children which are under artificial ventilation over a long period of time e.g. to treat infant respiratory distress syndrome (IRDS), are also at risk to develop BPD. On the one hand, the development of BPD is the result of reorganization processes with an inflammatory formation of connective tissue after an initial water retention in a premature lung which is exposed to chemical (oxygen radicals), mechanical (pressure trauma, volume trauma), and biological (microbial agent) damages. On the other hand, BPD of very early preterm infants which are born in a gestation age of less than 28 weeks is in particular characterized by a disorder or an arrest of the formation of the alveoli where the entire area of diffusion for the oxygen and the carbon dioxide is reduced. In addition to the pulmonary alveoli the respiratory tract is also affected, which becomes narrowed and, as a consequence, increases the airway resistance and the blood vessels of the lung, which may cause due to the vasoconstriction an increased pressure in the pulmonary circulation and a strain on the right ventricle.

Clinical symptoms of BPD may be an increased breathing rate, deeper, enforced breathing with contractions in the chest, increased bronchosecretion, growth retardation and livid skin and mucosa. In the X-ray image of the lung inter alia areas of overblowing next to areas with unsufficient ventilation and a fibrotic connective tissue reconstruction can be found. Diagnosis and classification is made on the basis of the oxygen requirement which is necessary at a certain age of the child for a sufficient oxygen saturation of the blood. A distinction is made between a mild, moderate, and a severe progressive form.

Current measures for the prophylaxis of BPD are the avoidance of preterm birth, so called induction of lung maturation before the birth with the administration of glucocorticosteroids to the mother, avoidance of infections, mild and preferably short term ventilation by even accepting increased carbon dioxide blood gas levels, early diagnosis and closure of an open ductus arteriosus and, if applicable, inhalative or systemic administration of glucosteroids or vitamin A to the child.

Currently an existing BPD is treated by the administration of oxygen to maintain the physiological oxygen saturation of the blood. Corticosteroids counteract the chronic inflammatory process. Diuretic medications should treat a pulmonary edema. In case of a narrowing of the respiratory tract the inhalation of bronchospasmolytics may be considered. Vasodilating medications may decrease any increased pressure in the pulmonary circulation.

However, the current prophylactic and therapeutic measures against developmental disorders which are associated with preterm birth, in particular BPD, only lead to satisfactory results to a limited extent and are very often associated with a variety of side effects. For instance, the administration of glucocorticosteroids does often result in growth disorders, impaired brain development, hyperglycaemia, stomach ulcers and intestinal bleeding, the development of osteoporosis etc.

SUMMARY OF THE INVENTION

Against this background it is the object of the present invention to provide a method for the prophylaxis and/or treatment of a developmental disorder which is associated with preterm birth in a preterm infant, by means of which the disadvantages known in the prior art are avoided or at least alleviated.

This object is met by the administration of a composition which comprises docosahexaenoic acid (DHA) and choline to a preterm infant.

The composition according to the invention can be a pharmaceutical or medicinal composition, respectively. It is to be understood that the composition according to invention can comprise a pharmaceutically acceptable formulation. Pharmaceutically acceptable formulations are well-known in the prior art. By the way of example, it is referred to the treatise of Kibbe A. (2000), Handbook of Pharmaceutical Excipients, 3rd edition, American Pharmaceutical Association and Pharmaceutical Press. Furthermore, the pharmaceutical composition according to the invention may comprise additives. They include any compound or composition which may be advantageous for the use according to the invention, which encompass salts, binders, solvents, dispersing agents and further compounds which are usually used in connection with the formulation of medicaments.

The composition according to the invention may also be a food supplement composition. It is to be understood that the composition according to the invention may comprise a formulation which is acceptable in the field of food stuff. Food stuff formulations are well known in the prior art.

The composition can be provided in form of a suspension or suspendable dry composition, an emulsion or any other appropriate preparation.

According to an embodiment the composition according to the invention may comprise DHA and choline as the only active agent, however, according to another embodiment it may also comprise further active agents.

Docosahexaenoic acid (DHA) is a polyunsaturated fatty acid. It belongs to the class of omega-3-fatty acids. DHA is also referred to as all-cis-docosa-4,7,10,13,16,19-hexaenoic acid and has the lipid name 022:6-ω-3. It has the molecular formula of $O_{22}H_{32}O_2$ and the CAS number 6217-54-5. In the composition according to the invention the DHA can for example be provided as a neutral lipid.

Choline is a primary monohydric alcohol and a quaternary ammonium compound. It is also referred to as 2-hydroxy-N,N,N-trimethylethan-amonium. It mostly exists as choline chloride and has the molecular formula of $C5H14ClNO$ and the CAS number 67-48-1. In the composition according to the invention the choline can be provided for example as salt, for instance as chloride salt.

According to the invention DHA and/or choline can be comprised exclusively in free form. According to an alternative variant DHA and/or choline may exclusively or additionally be comprised in bound form. Examples of bound forms of choline are sphingomyelin or phosphatidyl choline (lecithin) and arachidonic acid containing phosphatidyl choline (ARA-PC). DHA and/or choline can also exist in the composition according to the invention in bound form as DHA-containing phosphatidyl choline (DHA-PC).

According to the invention developmental disorders which are associated with preterm birth are to be understood as physical and/or cognitive developmental restrictions or retardation of the preterm infant which are closely associated with its biological maturation.

According to the invention a prophylaxis and/or treatment comprises the administration of the composition to the preterm infant.

The findings of the inventors were surprising. In the prior art the administration of docosahexaenoic acid (DHA) for the prophylaxis and treatment of developmental disorders, which are associated with preterm birth, is described, wherein the administration is mostly made to the pregnant mother.

Currently a study in Australia and New Zealand is carried out where the effects on the BPD of an administration of DHA to newborns should be investigated; trial ID ACTRN12612000503820, public title: Can omega 3 fatty acids improve respiratory outcomes in preterm infants, date submitted Aug. 5, 2012.

The administration of a combination of DHA and choline is neither described nor rendered obvious in the prior art.

The object underlying the invention is herewith completely met.

According to an embodiment of the invention the composition is administered to such a preterm infant with a gestational age of 30 weeks.

The gestational age is to be understood as the time period from the first day of the last menstruation of the mother until the birth of the child. This corresponds to the length of pregnancy and serves as the reference value for the physical and cognitive development of the infant.

This measure according to the invention has the advantage that such a composition is provided which effectively gives remedy to preterm infants at a particular risk, and which can counteract developmental disorders which are associated with preterm birth.

According to an embodiment of the invention the developmental disorder which is associated with preterm birth is such of the lung, the brain and/or the eye.

This measure has the advantage that the composition is configured for the prophylaxis and/or treatment of disruptions of such organs, the development of which is of particular relevance for the recovery of the child.

According to an embodiment of the invention the developmental disorder which is associated with preterm birth is selected from the group consisting of: bronchopulmonary dysplasia (BPD), intelligence deficits, cerebral palsy, white matter disease, retinopathy of preterm infants.

This measure has the advantage that the composition according to the invention can be used in such developmental disorders which are associated with preterm birth, which appear more frequently in preterm infants and so far cannot be treated in a satisfactory manner.

According to an embodiment the composition according to the invention additionally comprises arachidonic acid (ARA) and/or a precursor thereof.

Arachidonic acid (ARA) is a fourfold unsaturated fatty acid. It is also referred to as 5Z,8Z,11Z,14Z-eicosatetraenoic acid, Z,Z,Z,Z-eicosa-5,8,11,14-tetraenoic acid and has the lipid name 20:4(ω-6). ARA has the molecular formula of $C_{20}H_{32}O_2$ and the CAS number 506-32-1. It has a molecular weight of 304.46 g mol$^{-1}$. Arachidonic acid is synthesized in the animal organism from the essential omega-6-fatty acid linoleic acid via the intermediates γ-linolenic acid (GLA) and dihomo-γ-linolenic acid (DGLA) and intermediates. The precursors include any compounds which enter as a starting product into reactions of the synthetic pathway of ARA.

According to this embodiment of the invention ARA may be contained exclusively in free form. According to an alternative embodiment ARA is exclusively or additionally contained in bound form. An example of a bound form of ARA is ARA-containing phosphatidyl choline (ARA-PC).

The inventors have realized that the triple combination of DHA, choline, and ARA/precursor can counteract or therapeutically treat, in a particularly well manner, such developmental disorders, which are associated with preterm birth. For these nutrients the development of a post natal deficiency was demonstrated by the inventors by means of analysis from umbilical cord plasma, and residues of clinically indicated blood samples.

In this context according to an embodiment of the invention said composition may contain DHA, choline and ARA/precursor as the only active agents, however according to another embodiment it may also contain additional active agents.

According to another embodiment of the invention the precursor of ARA is all-cis-eicosa-8,11,14-trienic acid (DHGL; lipid name 020:3-ω-6).

The inventors have realized that such a precursor can be metabolized by the premature baby and for this reason provides particularly good results.

According to another embodiment of the invention said composition comprises the ratio of DHA:choline:ARA/precursor of approx. 1:1:1 up to approx. 1:2:2.

The inventors have realized that these concentration ratios result in a composition which can counteract developmental disorders, which are associated with preterm birth, or by which developmental disorders which are associated with preterm birth, can both be treated and counteracted in a very effective manner.

In this context the range of 1:1:1 to 1:2:2 includes all ratios where the relative proportions of choline and ARA/precursor in relation to DHA are in a ratio within the range of 1 to 2, thus, for example, each independent from another is 1, 1.1, 1.2, 1.3, 1.4, 1.5, 1.6, 1.7, 1.8, 1.9 or 2. "Approx." includes deviations of ±10%.

According to a preferred embodiment the composition is configured for an enteral, parenteral and/or oral administration.

This measure has the advantage that the composition is provided in such a form which is particularly suited for an administration to the preterm infant.

For an enteral administration the following galenics are possible:
(a) phosphatidyl choline which contains ARA and DHA as fatty acids;
(b) phosphatidyl choline which does not contain ARA and DHA in a significant quantity, supplemented by ARA- and DHA-containing triglyceride emulsion;
(c) combination of (a) and (b);
(d) galenics analogous to (a) to (c), where ARA is in parts or completely replaced by an ARA-precursor, e.g. DGLA.

For a parental application the following galenics are particularly suited:
(a) choline as free salt, e.g. choline chloride, in combination with ARA and DHA-containing neutral lipids as suspension or suspendable dry galenics;
(b) choline as free salt, in combination with ARA and/or DHA-containing phospholipids in suspension or emulsion or as suspendable or emulsifiable dry galenics;
(c) combination of (a) and (b);
(d) combination analogous to (a) to (c), wherein ARA is replaced by an appropriate precursor of ARA, e.g. DHGL.

For an oral application e.g. the following galenics is suited:
(a) choline from free salt, e.g. choline chloride, in combination with ARA and DHA containing neutral lipids as suspension or suspendable dry substance;
(b) phospholipid mixture of oil/suspension/emulsion or emulsifiable/suspendable galenics,
(c) combination of (a) and (b), or
(d) combination analogous to (a) to (c), where ARA is replaced by an appropriate precursor of ARA, e.g. DHGL.

According to another embodiment of the invention said composition does not contain eicosapentaenoic acid (EPA) or only an amount of 30 wt.-% of the DHA content.

Eicosapentaenoic acid is also referred to as all-cis-eicosa-5,8,11,17-pentaenoic acid and has the lipid name $C20:5-\omega-3$. This measure has the advantage that it is complied with the recommendations of the expert commission "European Society for Paediatric Gastroenterology, Hepatology, and Nutrition Committee, ESPGHAN Committee on Nutrition" for the delivery of EPA in relation to DHA in preterm infant; cf. Agostoni C et al. (2010), Enteral nutrient supply for preterm infants: Commentary from the European Society of Paediatric Gastroenterology, Hepatology and Nutrition Committee on Nutrition. J. Pediatr. Gastroenterol. Nutr. Vol. 50(1), p. 85-91.

Another subject matter of the present invention relates to the use of a combination of docosahexaenoic acids (DHA) and choline, and preferably additionally arachidonic acid (ARA) and/or a precursor thereof, for the prophylaxis and/or treatment of developmental disorders which are associated with preterm birth, preferably such which is selected from the group consisting of: bronchopulmonary dysplasia (BPD); intelligence deficits, cerebral palsy, white matter disease; retinopathy of prematurity.

The configurations, further developments, features, characteristics and advantages of the composition according to the invention apply likewise to this use according to the invention.

Another subject matter of the present invention relates to the use of the ratio of arachidonic acid (ARA)-phosphatidyl choline (PC):docosahexaenoic acid (DHA)-phosphatidyl choline (PC) for the diagnosis and/or determination and/or prediction of the degree of severity of a developmental disorder which is associated with preterm birth, preferably such which is selected from the group consisting of: bronchopulmonary dysplasia (BPD); intelligence deficits, cerebral palsy, white matter disease; retinopathy of prematurity.

The inventors have realized for the first time that the ratio of ARA-PC:DHA-PC is correlated with the degree of severity of a developmental disorder, in particular BPD, in preterm infants. The lower the ratio, preferably in the umbilical cord plasma, the higher the degree of severity which develops. Therefore, the ratio of ARA-PC:DHA-PC is inversely correlated with the degree of severity of the developmental disorder in preterm infants.

The configurations, further developments, features, characteristics and advantages of the composition according to the invention likewise apply to this use according to the invention.

For this reason, another subject matter of the present invention relates to a method for the diagnosis and/or determination and/or prediction of the degree of severity of a developmental disorder which is associated with preterm birth, which comprises the following steps:
(1) provision of a plasma sample of a preterm infant, preferably from the umbilical cord blood;
(2) determination of the ratio of arachidonic acid (ARA)-phosphatidyl choline (PC): docosahexaenic acid (DHA)-phosphatidyl choline (PC) in a plasma sample, preferably in umbilical cord plasma;
(3) inverse correlation of the ratio of ARA-PC:DHA-PC with the degree of severity of a developmental disorder which is associated with preterm birth.

The plasma sample of the preterm infant originates preferably from the umbilical cord blood. It can also originate from a "normal" blood sample, which is e.g. obtained during a newborn treated in hospital.

It is to be understood that the before-mentioned features and those to be mentioned in the following cannot only be used in the combination indicated in each case but also in other combinations or in isolated position without departing from the scope of the invention.

The present invention is now explained in detail by means of embodiments from which further features, characteristics and advantages of the invention results. The embodiments are not limiting.

It is to be understood that individual features which are disclosed in the embodiments are not only disclosed in the context of the very specific embodiment but also in a generality and said features provide a contribution to the invention on their own. For this reason the skilled person can freely combine these features with other features of the invention.

BRIEF DESCRIPTION OF THE FIGURES

FIG. 1: Supply of preterm infants with enteral and parenteral choline (A) and fat (B). The data were calculated from individual patient files, and are indicated as medians (♦, Δ). Thick bars represent the 25th and 75th percentiles and thin bars represent the minimum and maximum values of a total of 93 (one case of death at day 27) patients. The dashed line in (A) defines the calculated median "adequate intake" (AI) of the study group (27.4 mg/kg/d), whereas the grey box defines the calculated AI values for 1200 g (25.2 mg/kg/d) and 290 g (31.4 mg/kg/d) weight at birth weight.

FIG. 3: Differential postnatal changes of polyunsaturated phosphatidyl choline (PC; A) and phosphatidyl ethanolamine (PE; B) subgroups in preterm infants. Data are from 171 individual measurements in preterm infants which were treated in hospital, and indicate the postnatal kinetics of PC and PE subgroups with long chain polyunsaturated fatty acids, namely arachidonic acid (ARA), eicosapentaenoic acid (EPA) and docosahexaenoic acid (DHA). The data for ARA-PE and EPA-PE fitted linear regression models. ARA-PC, EPA-PC, DHA-PC and DHA-PE deviate from linearity and followed a model of two distinct first order kinetics. For the latter, individual regression lines are depicted before and after the respective breakpoints. Abbreviations: r, correlation coefficient; p, significance level.

FIG. 5: Correlation between maternal and fetal PC subgroups throughout pregnancy (24-42 weeks postmenstrual age). The concentrations (A,B) and percentages (C,D) between 121 umbilical cord blood plasma (fetal) and the corresponding maternal blood sera (parturient). Abbreviations: Sat.-PC, saturated PC; C18:1-PC, oleic acid containing PC; C18:2-PC, linoleic acid containing PC; ARA-PC, arachidonic containing PC; EPA, eicosapentaenoic acid containing PC; DHA-PC, docosahexaenoic acid containing PC; PC, phosphatidyl choline; r, correlation coefficient; p, significance level.

DESCRIPTION OF PREFERRED EMBODIMENTS

The invention relates to the treatment and prevention of developmental disorders of preterm infants, which are associated with preterm birth, in particular the bronchopulmonary dysplasia (BPD), by the application of a combined substitution von nutrients which are involved in the structure formation and functionality of parenchymatic organs in a fundamental manner. They include choline [2-hydroxy-N,N,N-trimethyl-ammonium], arachidonic acid (ARA) [all-cis-eicosa-5,8,11,14-tetraenoic acid; C20:4-ω-6] and docosahexaenoic acid (DHA) [all-cis-docosa-4,7,10,13,16,19-hexaenoic acid; C22:6-ω-3].

For these nutrients the inventors showed by means of an analysis of umbilical cord plasma and residues of clinically indicated blood samples the development of a postnatal deficiency. For choline a rapid postnatal decrease in concentration of approximately 50% of the fetal plasma concentration was demonstrated. For the choline-containing plasma phospholipid of phosphatidyl choline (PC) breakpoint analyses showed that the percentage of ARA and DHA-containing components in relation to the entire PC decreases by approximately 50% within 3 (ARA-PC) or 5.7 (DHA-PC) days. Therefore, this happened with preterm infants at an unphysiologically early point in time. In addition, ARA-PC further decreases during the treatment in hospital.

Analyses of umbilical cord plasma of very early preterm infants (24-28 weeks post conceptual age) showed that an initially low ratio of ARA-PC to DHA-DC is associated with the development and the degree of severity of the bronchopulmonary dysplasia (BPD). Therefore a low ratio of ARA-PC/DHA-PC at the birth predisposes for the development of the BPD or allows a prediction of the postnatal BPD development.

For this reason, the inventors have realized that by an early substitution of DHA and choline and, if applicable, additionally of ARA or their appropriate precursors in appropriate combination and dosage the formation of developmental disorders which are associated with preterm birth, in particular BPD, can be prevented. The supply of the composition according to the invention can be realized both per os in the context of the oral restorative diet and—e.g. in case of a clinically conditioned delay or interruption of this restorative diet—by the supply of an enteral or parenteral choline-, ARA- and DHA-containing emulsion/dispersion.

The phospholipide and choline analytics by means of tandem mass spectrometry allowed the inventors to examine the choline, DHA and ARA metabolism and its homeostasis in a targeted and differentiated manner.

With the invention it will be possible to prevent developmental disorders which are associated with preterm birth, in particular the frequent and chronic pathology of the bronchopulmonary dysplasia (BPD) of extremely small preterm infants (<30 weeks gestational age). The BPD is a serious pathology which in individual cases may result in death and in the majority of the cases it is associated with a long-lasting disorder of the lung function and the neurocognitive development.

It was realized by the inventors for the first time that there is a significant correlation between the addressed lipid metabolic parameters (ARA-PC/DHA-PC ratio) and the clinical pathology of the BPD in preterm infants, so that the descriptive lipid biochemistry results in a clinically applicable concept of the prophylaxis and treatment of developmental disorders which are associated with preterm birth, in particular the BPD.

Furthermore it was also realized for the first time that a nutrient combination based on the high demand of the preterm infant and the metabolism of long chain polyunsaturated fatty acids which are essential to fetus (ARA, DHA) can be used for the prevention of developmental disorders which are associated with preterm birth, in particular the bronchopulmonary dysplasia (BPD). The metabolism of ARA and DHA is coupled to the one of choline which results in a reasonable triple combination.

Furthermore, it was realized for the first time that a prediction of developmental disorders, in particular of BPD, is enabled by a measurement of the ratio of ARA-PC/DHA-PC in the umbilical cord blood or in the first days of life, which allows a targeted treatment or prevention of treatment side effects in children with low risk.

The advantages of the invention lie in the fact that the problem of inadequate development of preterm infants, in particular of their lung, is addressed by a targeted and adapted and combined administration of the precursors which are essential for the metabolism and the structure formation of the premature lung, however which are not sufficiently supplied to preterm infants, as it was now discovered.

An effective nutritive instrument of the BPD prophylaxis constitutes a major progress in the treatment of extremely immature preterm infants, which has not been solved in a satisfactory manner by any previous pharmacological approaches. The combined administration of choline, DHA and, if applicable, ARA (and/or its precursors DHGL), is therefore a significant instrument in the prophylaxis of developmental disorders which are associated with preterm birth, in particular the BPD, and the replacement of/complement to anti-inflammatory therapeutics (catabolically and especially in preterm infants cerebro- and cerebello toxically effective glucocorticoids) and other pharmaceuticals.

Figure 1:
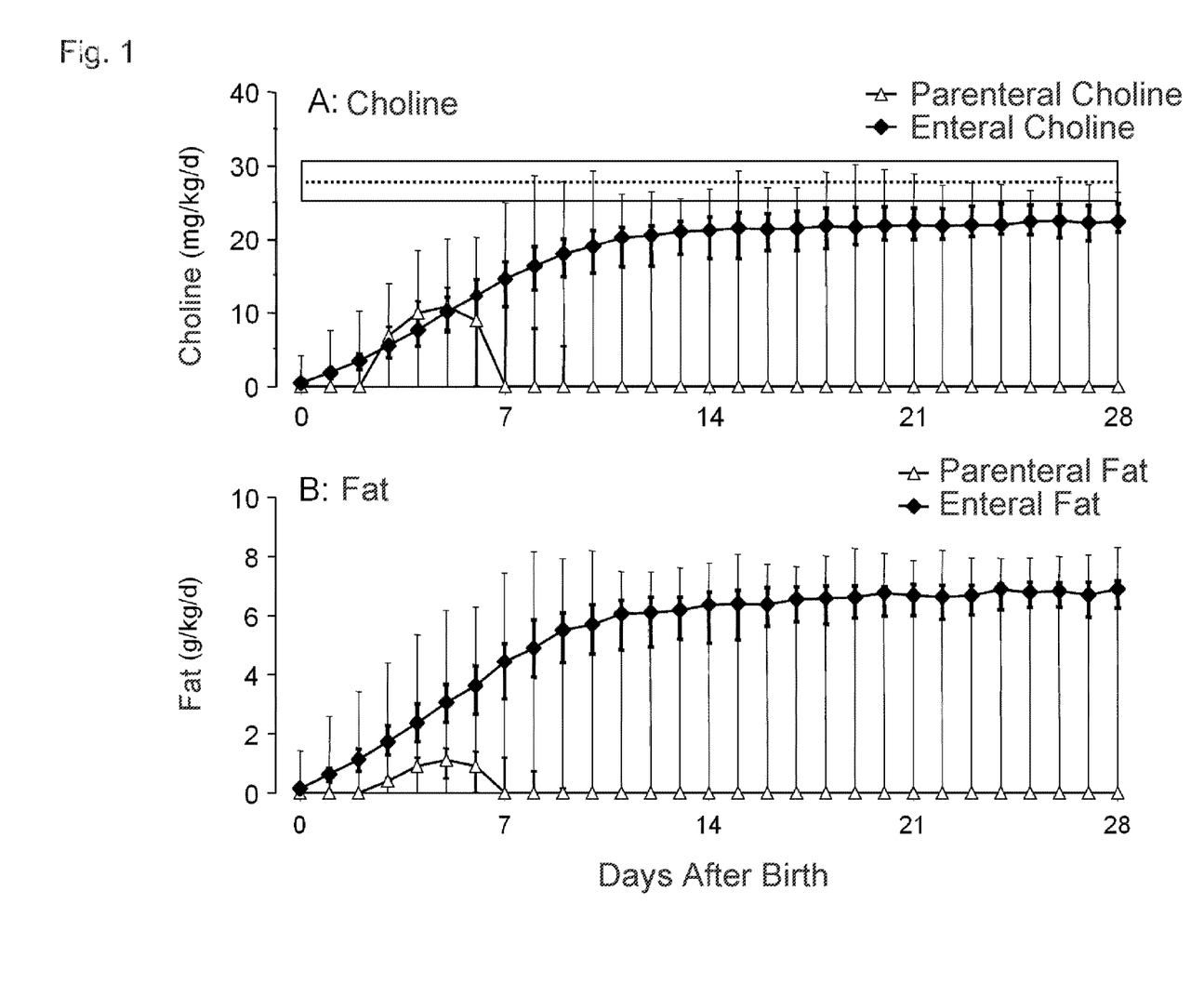
Figure 2:
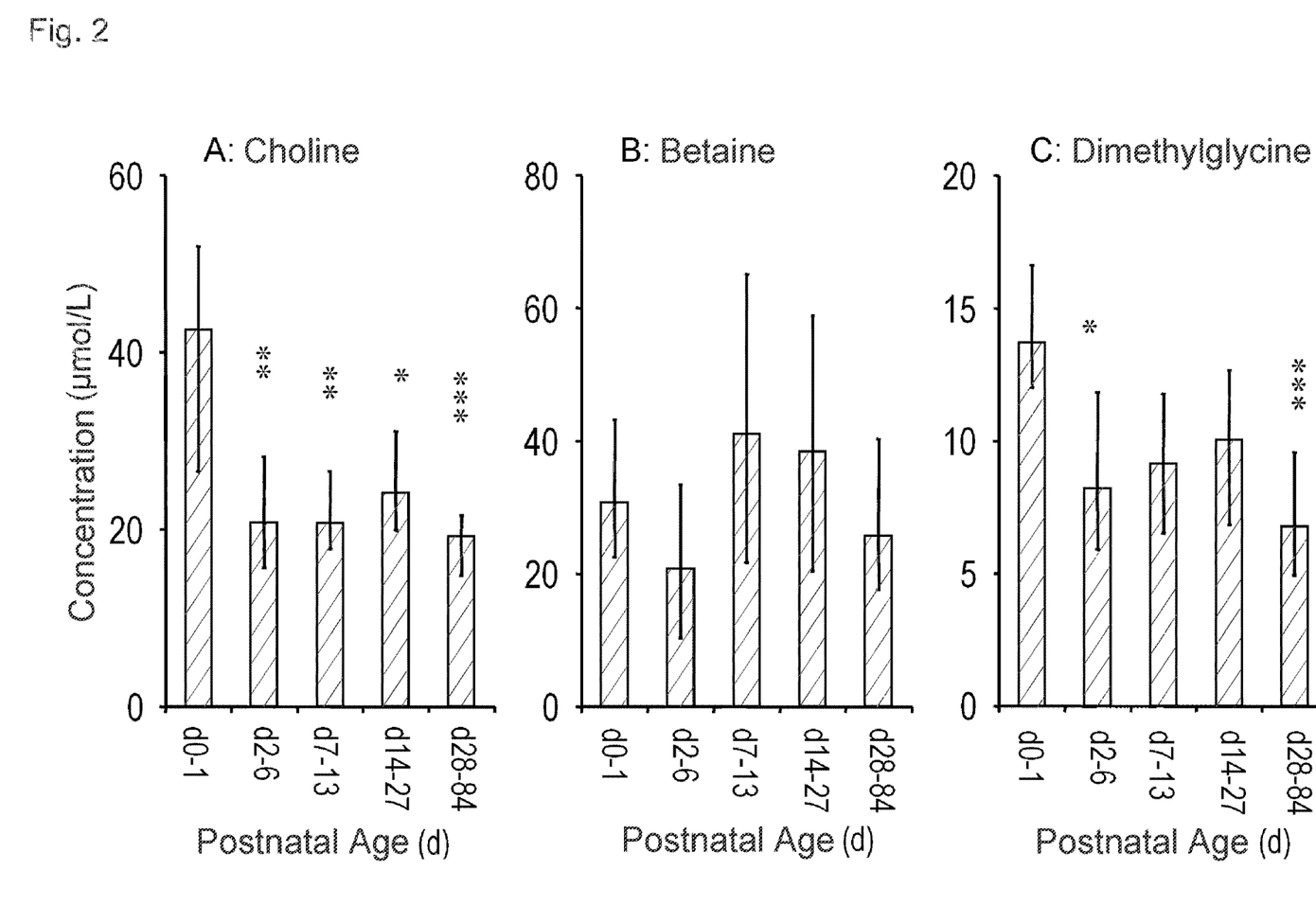
FIG. 2: Postnatal changes in the plasma concentrations of choline (A), betaine (B) and dimethylglycine (C) in preterm infants. The data are indicated as medians and 25th/75th percentiles of n=13 (postnatal day d0-1), n=30 (d2-6), n=23 (d7-13), n=43 (d14-27) and n=53 (d28-84) postnatal plasma samples of preterm infants treated in hospital. The statistical analyses were performed by using the non-parametric Dunn test for group comparisons. Abbreviations: *, $p<0.05$, , $p<0.01$, *, $p<0.001$ compared to postnatal age d0-1.
Figure 3:
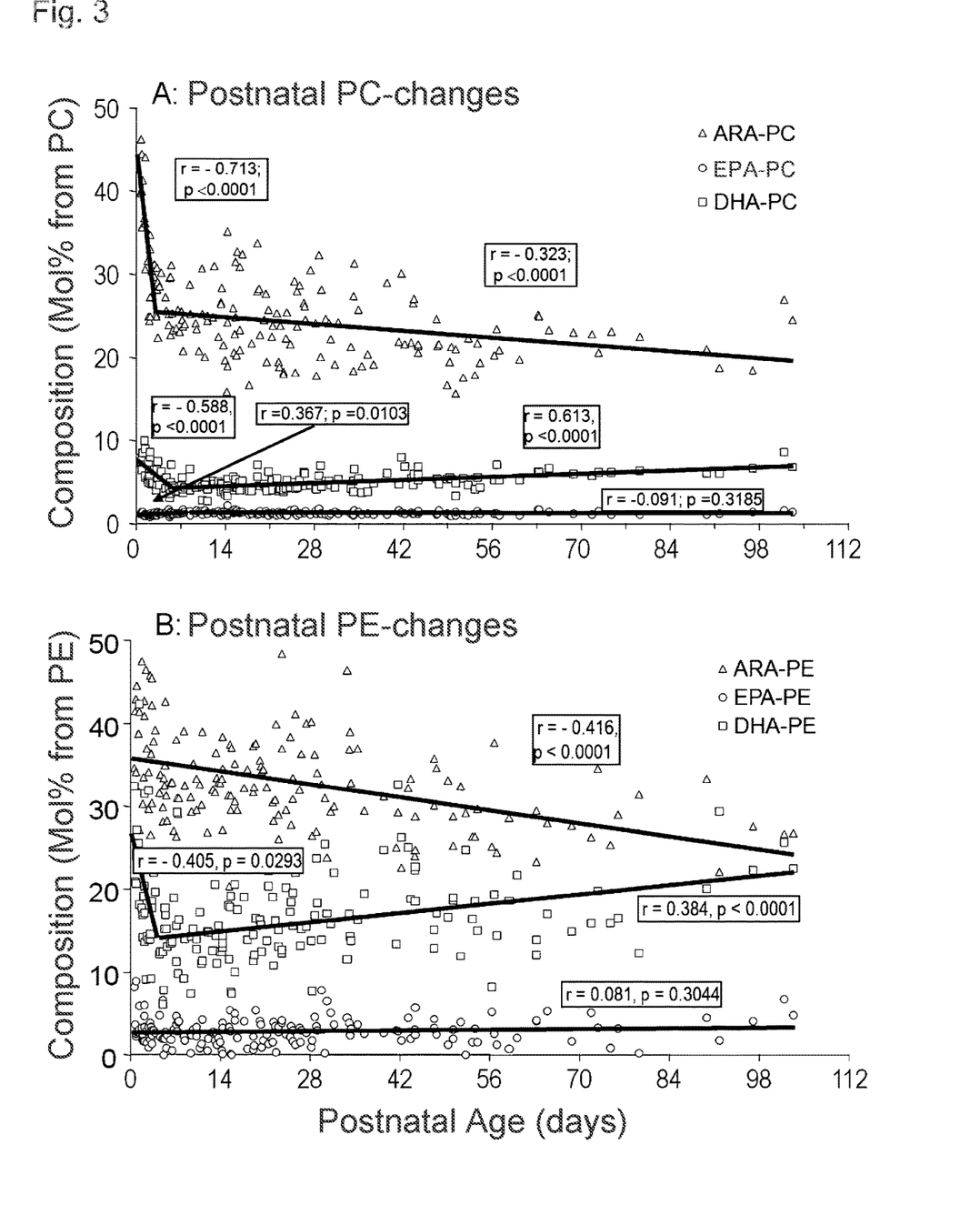

The inventors have carried out in the past investigations of the choline and phosphatidyl choline (PC) homeostasis in mothers (perinatal blood serum), fetuses (umbilical cord blood plasma) and in preterm infants treated in hospital (24-42 weeks postmenstrual gestation age (PMA)). The investigations showed that the choline supply of preterm infants is not sufficient and, in particular, discontinuous, in contrast to the situation in utero (FIG. 1; from Bernhard et al. (2013; l.c.)). The investigations of the inventors also show that the concentration of choline in plasma post partum decreases within 48 hours to 50% of the physiological value which means—for a high Michaelis constant of non-synaptic choline carrier—a halving of the tissue intake (FIG. 2; from Bernhard et al. (2014), Eur. J. Nutr. of Aug. 23, 2014, l.c.). In the same way the percentage of the ARA- and DHA-containing phospholipids, in particular of the choline-containing phosphatidyl choline (PC) is reduced by approximately 50% within 3 (ARA-PC) or 5.7 (DHA-PC) days post partum. These values do not normalize postnatal (ARA-PC) or do so only substantially delayed (DHA-PC) to the values which correspond to the postconceptional age (FIG. 3; Bernhard et al. 2014), Eur. J. Nutr. 53(7):1533-47).

New pair analyses of phospholipids of umbilical cord plasma and maternal serum were carried out and in particular (1) the dependency between the maternal and fetal phospholipid state was determined, and (2) its relation to the bronchopulmonary dysplasia (BPD), the most frequent long lasting vegetative impairment of former preterm infants, was analyzed.

Figure 4:
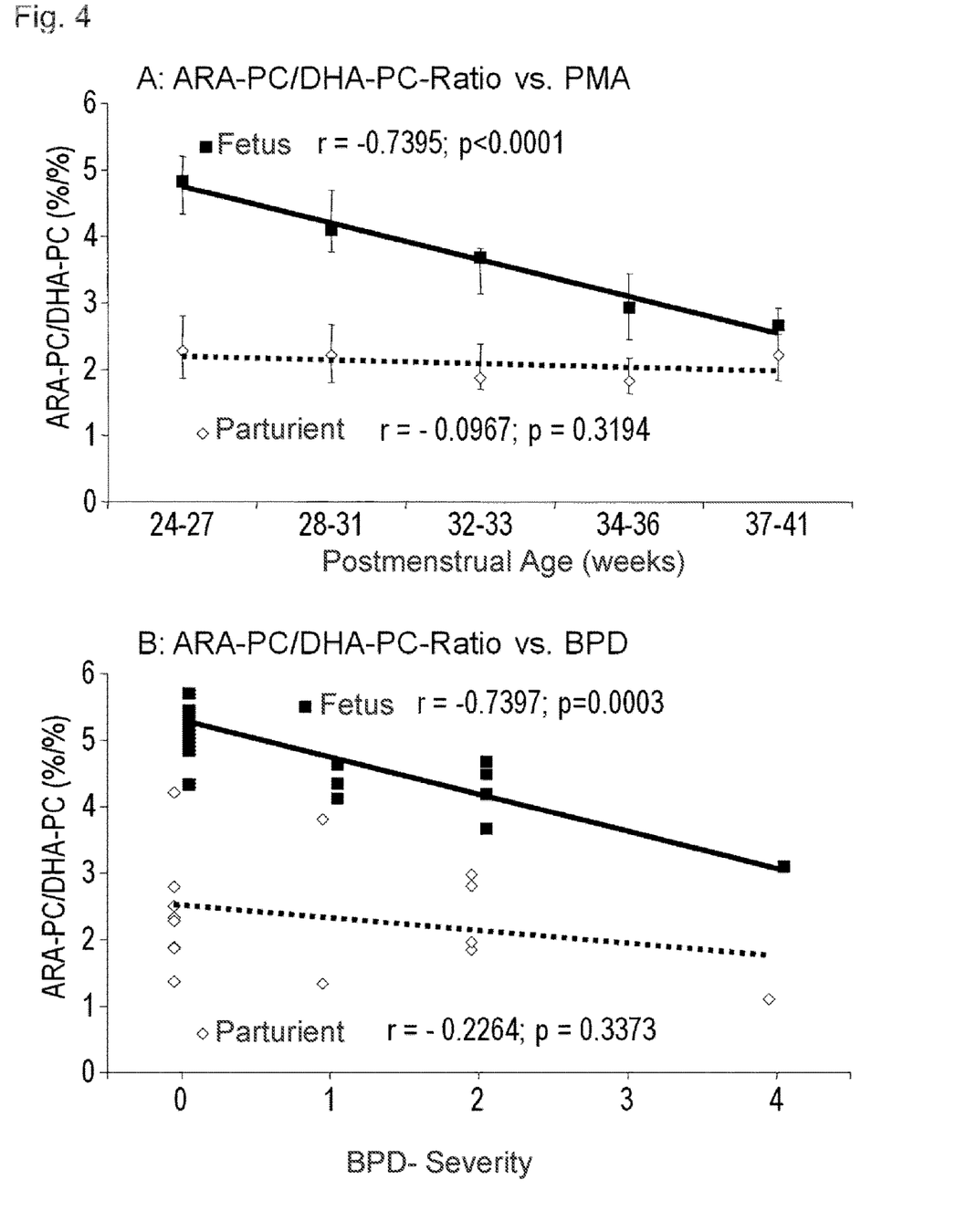
FIG. 4: Changes in the fetal and maternal ARA-PC to DHA-PC ratio relative to the postmenstrual age of the fetus (A) and the degree of severity of the development of bronchopulmonary dysplasia (B). The ratios of ARA-PC to DHA-PC were determined from their respective concentrations in umbilical cord plasma (fetus) and maternal serum at the time of birth. Data in A indicate medians and 25th/75th percentiles in relation to the postmenstrual age, while data in B show individual measured points of patients with a high risk for BPD (below 28 weeks postmenstrual age at birth; N=34) and the linear regression line after testing for linearity. Abbreviations: PMA, postmenstrual age; r, correlation coefficient; p, significance level.

It has been found that the ratio of ARA-PC to DHA-PC in particular in very small preterm infants is high (FIG. 4A). It further has been surprisingly found that a low ARA-PC/DHA-PC ratio correlates with the incidence and the degree of severity of the BPD (r=−0.7397; p=0.0003) (FIG. 4B).

Figure 5:
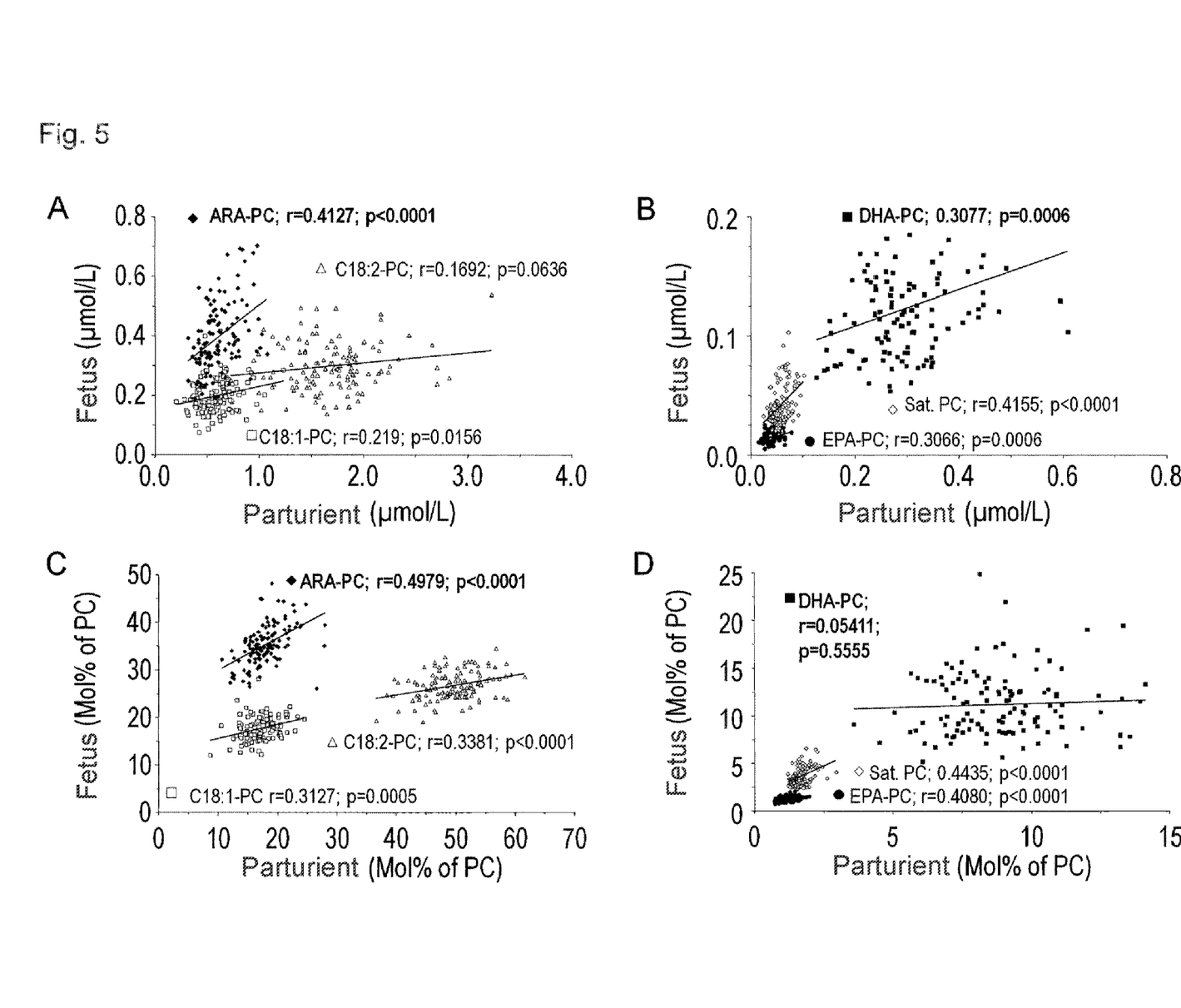

The comparison of maternal and fetal PC further showed that the initial neonatal concentrations of ARA-PC and DHA-PC correlate with maternal values, so that the target group of very immature preterm infants is born with different levels of ARA and DHA "load" (FIG. 5).

In addition to these results it has been demonstrated that the measurement of the ARA-PC/DHA-PC ratio provides a new predicative parameter.

What is claimed is:

1. A method for the prophylaxis and treatment of bronchopulmonary dysplasia (BPD) in a preterm infant, the method consisting of administering to said preterm infant a composition consisting of docosahexaenoic acid (DHA), choline, arachidonic acid (ARA), and optionally a pharmaceutically acceptable excipient.

2. The method of claim 1, wherein said preterm infant has a gestational age of ≤30 weeks.

3. A method for the prophylaxis and treatment of bronchopulmonary dysplasia (BPD) in a preterm infant, the method consisting of administering to said preterm infant a composition consisting of docosahexaenoic acid (DHA), choline, arachidonic acid (ARA) or a precursor thereof, and optionally a pharmaceutically acceptable excipient.

4. The method of claim 3, wherein the precursor of ARA is all-cis-eicosa-8,11,14-trienic acid (DHGL).

5. The method of claim 3, wherein in said composition the ratio of DHA:choline:ARA/precursor is about 1:1:1 up to about 1:2:2.

6. The method of claim 1, wherein said composition is configured for an enteral, parenteral and/or oral administration.

7. The method of claim 1, wherein said composition is a pharmaceutical composition.

8. The method of claim 1, wherein said composition is a food supplemental composition.

* * * * *

UNITED STATES PATENT AND TRADEMARK OFFICE
CERTIFICATE OF CORRECTION

PATENT NO. : 10,898,454 B2  
APPLICATION NO. : 15/663483  
DATED : January 26, 2021  
INVENTOR(S) : Wolfgang Bernhard et al.

Page 1 of 1

It is certified that error appears in the above-identified patent and that said Letters Patent is hereby corrected as shown below:

On the Title Page

In Column 2, Item (56), Line 10, under Other Publications, delete "Gastrenterology" and insert -- Gastroenterology --.

In the Specification

In Column 3, Line 24, delete "022:6" and insert -- C22:6 --.

In Column 3, Line 25, delete "022H3202" and insert -- C22H32O2 --.

In Column 3, Line 30, delete "amonium." and insert -- ammonium. --.

In Column 4, Line 3, delete "30" and insert -- ≤30 --.

In Column 4, Line 67, delete "020" and insert -- C20 --.

In Column 5, Line 52, delete "galenics," and insert -- galenics; --.

In Column 5, Line 53, delete "(b), or" and insert -- (b); or --.

In Column 5, Line 58, delete "30" and insert -- ≤30 --.

In Column 8, Line 43, delete "phospholipide" and insert -- phospholipid --.

In Column 10, Line 2, delete "47)." and insert -- 47. --.

Signed and Sealed this  
Fourth Day of May, 2021

Drew Hirshfeld  
*Performing the Functions and Duties of the*  
*Under Secretary of Commerce for Intellectual Property and*  
*Director of the United States Patent and Trademark Office*